United States Patent
Linn et al.

(10) Patent No.: US 11,304,912 B2
(45) Date of Patent: Apr. 19, 2022

(54) TRANSDERMAL THERAPEUTIC SYSTEM ON THE BASIS OF ADHESIVE PLASTICIZER-POLYMER MATRICES

(71) Applicant: LTS LOHMANN THERAPIE-SYSTEME AG, Andernach (DE)

(72) Inventors: Michael Linn, Waldböckelheim (DE); Markus Müller, Troisdorf (DE); Marius Bauer, Andernach (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 16/765,800

(22) PCT Filed: Nov. 21, 2018

(86) PCT No.: PCT/EP2018/082090
§ 371 (c)(1),
(2) Date: May 20, 2020

(87) PCT Pub. No.: WO2019/110306
PCT Pub. Date: Jun. 13, 2019

(65) Prior Publication Data
US 2020/0281867 A1 Sep. 10, 2020

(30) Foreign Application Priority Data
Nov. 21, 2017 (DE) .................... 10 2017 127 433.2

(51) Int. Cl.
*A61K 9/70* (2006.01)
*A61K 31/122* (2006.01)
(Continued)

(52) U.S. Cl.
CPC .......... *A61K 9/7069* (2013.01); *A61K 31/122* (2013.01); *A61K 31/135* (2013.01);
(Continued)

(58) Field of Classification Search
CPC .. A61K 31/24; A61K 31/4468; A61K 9/7069; A61K 31/216; A61K 31/4545;
(Continued)

(56) References Cited

U.S. PATENT DOCUMENTS

2003/0175328 A1 9/2003 Shefer et al.
2003/0175333 A1 9/2003 Shefer et al.
(Continued)

FOREIGN PATENT DOCUMENTS

DE 4237453 C1 8/1993
DE 69833000 T2 9/2006
(Continued)

OTHER PUBLICATIONS

Office Action for Japanese Application No. 2020-527938, dated Jul. 27, 2021, 5 pages.

*Primary Examiner* — Jianfeng Song
(74) *Attorney, Agent, or Firm* — Fay Sharpe LLP

(57) ABSTRACT

The present application relates to a transdermal therapeutic system comprising a backing layer impermeable to active substances and a polymer matrix on one side of the backing layer impermeable to active substances, wherein the polymer matrix comprises at least one pharmaceutically active substance, at least one inherently non-self-adhesive polymer and at least one plasticizer, said polymer matrix being free of adhesive polymers. The invention further relates to a method of producing the transdermal therapeutic system and to the use thereof as a drug.

16 Claims, 3 Drawing Sheets

(51) Int. Cl.
 *A61K 31/24*     (2006.01)
 *A61K 31/506*    (2006.01)
 *A61K 31/381*    (2006.01)
 *A61K 31/4545*    (2006.01)
 *A61K 31/135*    (2006.01)
 *A61K 31/663*    (2006.01)
 *A61K 31/4468*    (2006.01)

(52) U.S. Cl.
 CPC ............ *A61K 31/24* (2013.01); *A61K 31/381* (2013.01); *A61K 31/4468* (2013.01); *A61K 31/4545* (2013.01); *A61K 31/506* (2013.01); *A61K 31/663* (2013.01)

(58) Field of Classification Search
 CPC .. A61K 31/663; A61K 31/506; A61K 31/135; A61K 9/7076; A61K 31/122; A61K 31/381
 See application file for complete search history.

(56) References Cited

U.S. PATENT DOCUMENTS

| | | | |
|---|---|---|---|
| 2009/0010998 | A1 | 1/2009 | Marchitto et al. |
| 2009/0297591 | A1* | 12/2009 | Chiang ................ A61K 9/7061 424/449 |
| 2010/0100124 | A1* | 4/2010 | Calabrese .......... C08G 18/7614 606/214 |
| 2010/0209472 | A1* | 8/2010 | Wang ..................... A61L 31/16 424/423 |

FOREIGN PATENT DOCUMENTS

| | | |
|---|---|---|
| EP | 0195643 A2 | 9/1986 |
| EP | 0439180 A2 | 7/1991 |
| EP | 1557164 A1 | 7/2005 |
| WO | 0147503 A1 | 7/2001 |
| WO | 02008351 A1 | 1/2002 |
| WO | 03034900 A2 | 5/2003 |
| WO | 2008083149 A1 | 7/2008 |
| WO | 2008108209 A1 | 9/2008 |
| WO | 2012103016 A2 | 8/2012 |

\* cited by examiner

TRANSDERMAL THERAPEUTIC SYSTEM ON THE BASIS OF ADHESIVE PLASTICIZER-POLYMER MATRICES

The present application relates to a transdermal therapeutic system on the basis of adhesive plasticiser-polymer matrices, a method for production thereof, and use thereof as a medicinal product.

In recent years, transdermal therapeutic systems (TTS) have enjoyed widespread use as an administration form for the treatment of numerous diseases, since they are associated with advantages in comparison to conventional administration forms. These advantages lie, amongst other things, in a precise and constant active substance delivery, which is necessary for a constant concentration of the active substance in the blood plasma. In addition, the first-pass effect can be avoided and the compliance increased, since the patient does not have to take tablets at regular intervals. One advantage of transdermal therapeutic systems in comparison to other topical application systems, such as salves or creams, also lies in the fact that these systems can be applied over a specific area and therefore offer precise dosage; furthermore, the risk of a salve being wiped off accidentally or other points of the skin being contaminated is eliminated.

Transdermal therapeutic systems as are known from the prior art generally comprise a backing layer impermeable to active substances and an active-substance-containing adhesive matrix layer. The adhesive matrix layer in the known transdermal therapeutic systems comprises at least one adhesive polymer in order to stick the transdermal therapeutic system to the patient's skin. These adhesive polymers, as are known from the prior art, generally comprise adhesive polymers on the basis of (meth)acrylate and/or on a silicone basis.

The transdermal therapeutic systems known from the prior art thus have the disadvantage that the compatibility of the pharmaceutically active substance with the adhesive polymers usually obtainable must be taken into consideration. This often leads to relatively complex and elaborate formulations, since a potential incompatibility between active substance and the usual adhesive polymers can be overcome only by the addition of further auxiliaries, for example further solvents and/or emulsifiers. In addition, methods for producing transdermal therapeutic systems comprising such complex and elaborate formulations are economically disadvantageous.

The aim of the present invention is therefore to provide a transdermal therapeutic system of which the matrix layer is sticky enough for the system to be adhered to the patient's skin, but does not comprise the usual adhesive polymers. In addition, active substances that are not soluble in the usual solvents that are normally used together with the usual adhesive polymers should also be suitable for administration by means of the transdermal therapeutic system. The matrix layer of the transdermal therapeutic system should additionally preferably comprise such polymers that have a especially broad compatibility spectrum with the wide range of different pharmaceutically active substances. The transdermal therapeutic systems thus obtained, however, should have similar properties in respect of the active substance permeation or the active substance flux as compared to the conventional transdermal therapeutic systems on the basis of adhesive polymers. Furthermore, an economically viable production method for a transdermal therapeutic system of this kind is to be provided.

The aim is achieved in accordance with the invention by a transdermal therapeutic system according to claim 1 which comprises a backing layer impermeable to active substances and a polymer matrix on one side of the backing layer impermeable to active substances, wherein the polymer matrix comprises at least one pharmaceutically active substance, at least one inherently non-adhesive polymer, and at least one plasticiser, characterised in that the polymer matrix is free of inherently adhesive polymers.

The polymer matrix might also consist only of the aforementioned constituents.

Especially, it has been found that, by combining inherently non-adhesive polymers with plasticisers, a polymer matrix is obtainable which has adhesive properties and thus can act as an adhesive in the transdermal therapeutic system. It is especially advantageous that polymers may be used which are compatible with a multitude of pharmaceutically active substances and that it is possible to dispense with the usual solvents, which normally are used together with the usual adhesive polymers. The problem of compatibility of pharmaceutically active substances and many of the usual inherently adhesive polymers may thus be avoided.

An inherently adhesive polymer is understood to mean a polymer that can act, by itself, as an adhesive, as defined in DIN EN 923:2016-03. An inherently non-adhesive polymer therefore, by itself, cannot act as an adhesive as defined above.

The polymer matrix of the transdermal therapeutic system according to the invention is free of inherently adhesive polymers.

Especially, no adhesive polymers on the basis of (meth)acrylate or poly(meth)acrylate, polyisobutylene, and/or adhesive polymers on the basis of silicone and/or copolymers thereof are contained in the transdermal therapeutic system according to the invention.

Plasticisers are liquid or solid, neutral organic substances, preferably with low vapour pressure, which, without chemical reaction, on account of their solubility and rate of swelling, but in some circumstances also without this, preferably physically interact with high-polymer substances and may form a homogeneous system therewith. Plasticisers impart certain sought physical properties onto the structures or coatings produced using them, for example lower freezing temperature, increased deformation capability, increased elastic properties, reduced hardness and possibly increased adhesion.

The backing layer impermeable to active substances is preferably insert and as flexible as possible so that the transdermal therapeutic system can also be applied to uneven areas of the skin. Any suitable material, such as polyethylene terephthalate, polyethylene, polybutylene, polyurethane and/or polyester, etc. may be used for the backing layer. The backing layer impermeable to active substances is preferably a polyethylene terephthalate film.

The transdermal therapeutic system according to the invention in a preferred embodiment comprises a removable protective layer on the side of the matrix layer on which the backing layer impermeable to active substance is not situated. The removable protective layer may be produced from various materials, such as polyethylene terephthalate, polyethylene and/or polypropylene, and is specially treated on the side in contact with the active-substance-containing polymer matrix so that it can be detached therefrom as easily as possible. The removable protective layer is advantageously formed on the basis of a polyethylene terephthalate layer.

The transdermal therapeutic system according to the invention is also characterised in that the transdermal therapeutic system does not comprise an additional adhesive layer, especially on the basis of adhesive polymers, on the side of the polymer matrix on which the backing layer impermeable to active substances is not situated.

This has the advantage that potential problems of compatibility with the at least one pharmaceutically active substance and the adhesive polymers of an additional adhesive layer may also be eliminated.

The transdermal therapeutic system according to the invention is also characterised in that the inherently adhesive polymer comprises a water-soluble polymer.

Water-soluble polymers comprise chemically very different, natural or synthetic polymers, whose common feature is their solubility in water or aqueous media. A precondition for this is that these polymers have number of hydrophilic groups sufficient for the water solubility and are not crosslinked. The hydrophilic groups may be non-ionic, anionic, cationic and/or zwitterionic.

The transdermal therapeutic system according to the invention is preferably characterised in that the inherently non-adhesive polymer comprises a polyvinyl caprolactam/polyvinyl acetate/polyethylene glycol copolymer. Further possible polymers comprise polyvinyl alcohol, a vinylpyrrolidone/vinyl acetate copolymer, cellulose derivatives, such as hydroxypropyl methylcellulose or hydroxypropyl methyl cellulose, starch or starch derivatives, shellac, alginic acid, galactomannan, carrageenan and other plant gums, pullulan, xanthan, pectin and other glucans, dextran, polyalkylene glycols, carboxyvinyl polymers and/or copolymers thereof.

A suitable polyvinyl caprolactam/polyvinyl acetate/polyethylene glycol copolymer is obtainable for example under the trade name "Soluplus" from BASF. A suitable polyvinylpyrrolidone is obtainable for example under the trade name "Kollidon VA 64" from BASF. These polymers have the advantage that they are compatible with a multitude of pharmaceutically active substances without difficulty and in addition are largely harmless for the patient.

The transdermal therapeutic system according to the invention is preferably characterised in that the at least one plasticiser comprises glycerol, polyethylene glycol, especially polyethylene glycol 200, sorbitol and/or tributyl citrate.

The at least one plasticiser especially, preferably comprises glycerol and/or polyethylene glycol 200.

Due to the use of a polymer matrix comprising at least one inherently non-adhesive polymer and at least one plasticiser, an adhesive polymer matrix can be provided which, preferably after drying, can be used as an adhesive layer in the transdermal therapeutic system according to the invention.

The transdermal therapeutic system according to the invention is preferably characterised in that the amount of the at least one inherently non-adhesive polymer in the matrix layer is approximately 50 to 90 wt. %, preferably approximately 55 to 85 wt. %, especially preferably approximately 60 to 80 wt. %, in relation to the total weight of the matrix layer.

In addition, the transdermal therapeutic system according to the invention is preferably characterised in that the amount of the at least one plasticiser in the matrix layer is approximately 5 to 50 wt. %, preferably approximately 10 to 30 wt. %, in relation to the total weight of the matrix layer.

The weight ratio in parts by weight of the at least one polymer to the at least one plasticiser is especially approximately 90 to 50 to approximately 10 to 50 parts by weight, preferably approximately 85 to 65 to approximately 15 to 35 parts by weight, especially preferably approximately 80 to 60 to approximately 20 to 40 parts by weight.

If too little or too much plasticiser is used, the mixture is either not sticky, or a workable material batch cannot be provided at all.

The selection of the at least one pharmaceutically active substance is not limited in principle, and any pharmaceutically active substance that is suitable for transdermal application may be used.

The transdermal therapeutic system according to the invention is preferably characterised in that the at least one pharmaceutically active substance is selected from the group consisting of idebenone, oxybutynin, riociguat, rotigotine, apixaban, ketamine, alendronate and/or fentanyl.

The amount of the at least one pharmaceutically active substance is preferably approximately 1 to 20 wt. %, preferably approximately 5 to 15 wt. %, in relation to the total weight of the matrix layer.

The application time for which the transdermal therapeutic system is intended is preferably at least approximately 12 hours, more preferably at least approximately 24 hours, and even more preferably at least approximately 48 hours. The active substance amount will be matched to the desired application time.

The transdermal therapeutic system according to the invention is preferably characterised in that the transdermal therapeutic system comprises at least one auxiliary selected from the group comprising dyes, emulsifiers, penetration enhancers, pH regulators, humectants, preservatives and/or antioxidants, preferably in each case in an amount of from 0.01 to 20 wt. % in relation to the total weight of the matrix layer.

The penetration enhancer is preferably selected from fatty acids and/or fatty acid esters, such as pentanoic acid, hexanoic acid, octanoic acid, nonanoic acid, decanoic acid, lauric acid, myristic acid, palmitic acid, stearic acid, arachidic acid, behenic acid, lignoceric acid, isovaleric acid, neoheptanoic acid, neononanoic acid, isostearic acid, oleic acid, palmitoleic acid, linolenic acid, vaccenic acid, petroselinic acid, elaidic acid, oleic acid, arachidonic acid, gadoleic acid, erucic acid, ethyl acetate, methyl propylate, butyl acetate, methyl valerate, diethyl sebacate, methyl laurate, ethyl oleate, isopropyl decanoate, isopropyl myristate (myristic acid isopropyl ester), isopropyl palmitate, isopropyl oleinate (oleic acid isopropyl ester), preferably oleic acid, lauric acid and/or myristic acid, especially preferably oleic acid, and/or fatty acid esters, preferably oleic acid isopropyl esters and/or myristic acid isopropyl esters.

The at least one antioxidant is preferably selected from alpha-tocopherol, ascorbyl palmitate and butylhydroxytoluene.

The present invention also relates to a method for producing a transdermal therapeutic system as defined above, comprising the steps of:

a) suspending the at least one pharmaceutically active substance in a suspension comprising a solvent on the basis of an organic solvent and/or water, at least one inherently non-adhesive polymer, and at least one plasticiser;

b) applying the suspension obtained from a) to a backing layer impermeable to active substances; and c) removing the solvent.

The solvent that is used in step a) is preferably water.

The present invention also relates to a transdermal therapeutic system obtainable by the above-described method.

The present invention also relates to a transdermal therapeutic system as described above or obtainable by the above-presented method for use as a medicinal product.

The preferred embodiments described in conjunction with the transdermal therapeutic system according to the invention also apply for the method according to the invention and for the use according to the invention.

Figure 1:
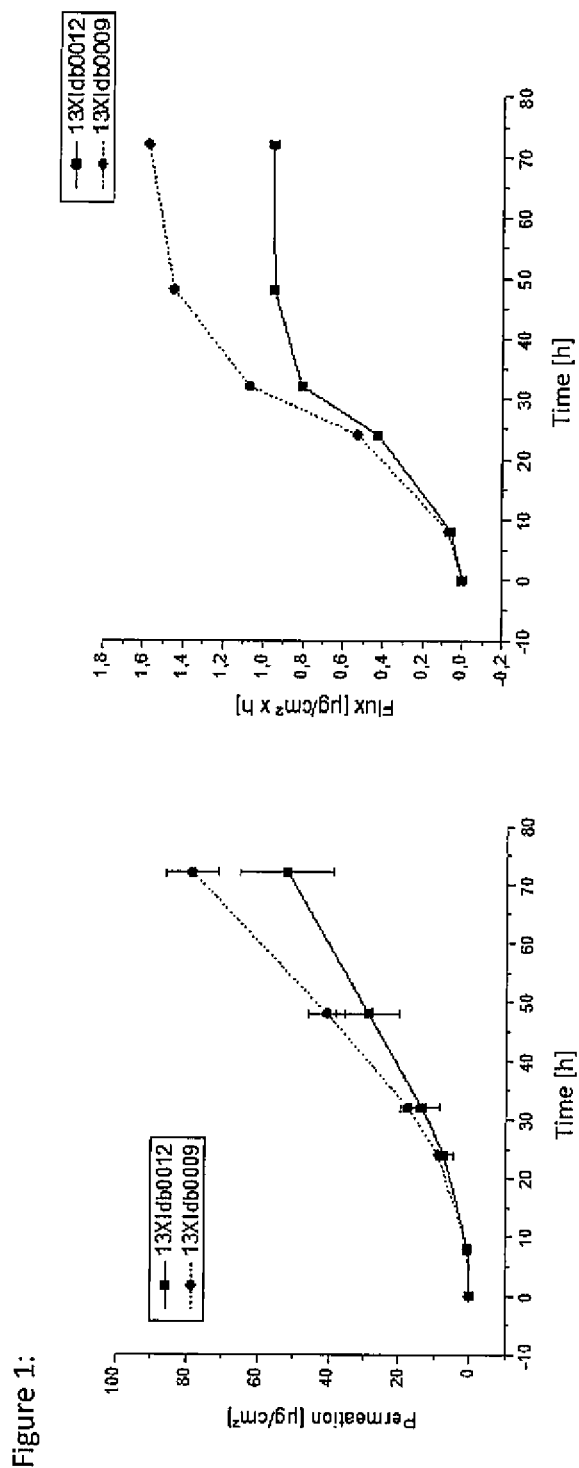
FIG. 1.

A transdermal therapeutic system according to the invention for administering idebenone according to the formulations in Table 1. The left-hand graph shows the cumulative active substance permeation, and the right-hand graph shows the active substance flux.

FIG. 2:

A transdermal therapeutic system comprising an adhesive on the basis of acrylate/silicone according to the prior art. The left graph shows the cumulative active substance permeation, and the right-hand graph shows the active substance flux.

FIG. 3:

A transdermal therapeutic system according to the invention for administering oxybutynin according to the formulations in Table 1. The left-hand graph shows the cumulative active substance permeation, and the right-hand GRAPH shows the active substance flux.

The invention will be explained hereinafter on the basis of non-limiting examples.

EXAMPLE 1

The following formulations were created and applied to a polyethylene terephthalate film. All formulations had adhesive properties.

TABLE 1

Formulations according to the invention

| Formulation code | Polymer | Plasticiser | Active substance |
|---|---|---|---|
| 124Idb0029 | 80% Soluplus | 10% PEG 200 | 10% Idebenone |
| 13XIdb0011 | 80% Soluplus | 10% Glycerol | 10% Idebenone |
| 13XIdb0012 | 70% Soluplus | 20% Glycerol | 10% Idebenone |
| 13XIdb0009 | 70% Kollidon VA 64 | 20% Glycerol | 10% Idebenone |
| 13XIdb0010 | 60% Kollidon VA 64 | 30% Glycerol | 10% Idebenone |
| 13XObu0001 | 70% Soluplus | 20% Glycerol | 10% Oxybutynin |
| 13XObu0002 | 70% Soluplus | 20% PEG 200 | 10% Oxybutynin |
| 13XObu0003 | 65% Soluplus | 25% PEG 200 | 10% Oxybutynin |
| 13XObu0004 | 60% Soluplus | 30% PEG 200 | 10% Oxybutynin |
| 13XObu0005 | 65% Kollidon VA 64 | 25% PEG 200 | 10% Oxybutynin |
| 13XObu0006 | 65% Kollidon VA 64 | 25% Glycerol | 10% Oxybutynin |
| 13XObu0007 | 65% Kollidon VA 64 | 25% PEG 200 | 10% Oxybutynin |
| 13XRio0004 | 60% Soluplus | 30% PEG 200 | 10% Riociguat |
| 13XRio0005 | 60% Kollidon VA 64 | 30% Glycerol | 10% Riociguat |
| 13XRio0006 | 60% Kollidon VA 64 | 30% PEG 200 | 10% Riociguat |
| 13XRio0007 | 60% Soluplus | 30% PEG 200 | 10% Riociguat |
| 13XRio0009 | 60% Soluplus | 30% Glycerol | 10% Riociguat |
| 13XRot0001 | 70% Soluplus | 20% Glycerol | 10% Rotigotine |
| 13XRot0002 | 70% Kollidon VA 64 | 20% Glycerol | 10% Rotigotine |
| 13XRot0003 | 75% Kollidon VA 64 | 15% Glycerol | 10% Rotigotine |

TABLE 2

Comparison formulations in conventional adhesives

| Formulation code | Polymer | Active substance |
|---|---|---|
| 13XIdb0001 | 90% DuroTak 4098 | 10% Idebenone |
| 13XIdb0002 | 90% DuroTak 2516 | 10% Idebenone |
| 13XIdb0003 | 80% DuroTak 4098 | 10% Idebenone |
| 13XIdb0004 | 90% DuroTak 2353 (80% neutralised) | 10% Idebenone |
| 13XIdb0005 | 90% DuroTak 2353 | 10% Idebenone |
| 13XIdb0006 | 90% Bio-PSA 4207 | 10% Idebenone |
| 13XIdb0007 | 1st coat 90% Bio-PSA 4107 2nd coat 10% Enhancer mix (35% miglyol, 25% dimethyl isosorbide, 25% eucalyptol, 15% n-dodecanol) Bio-PSA 4602 | 10% Idebenone (in the 1st coat) |
| 13XIdb0008 | 92.5% Bio-PSA 4602 | 7.5% Idebenone |

Figure 2:
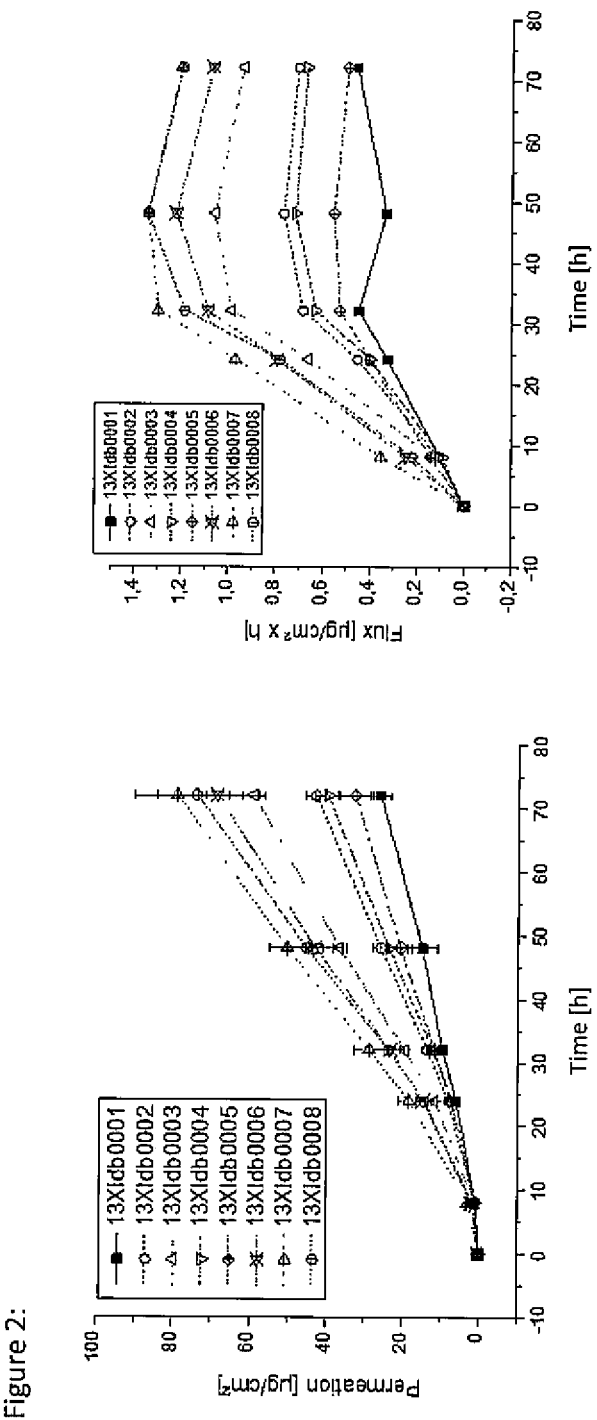
Figure 3:
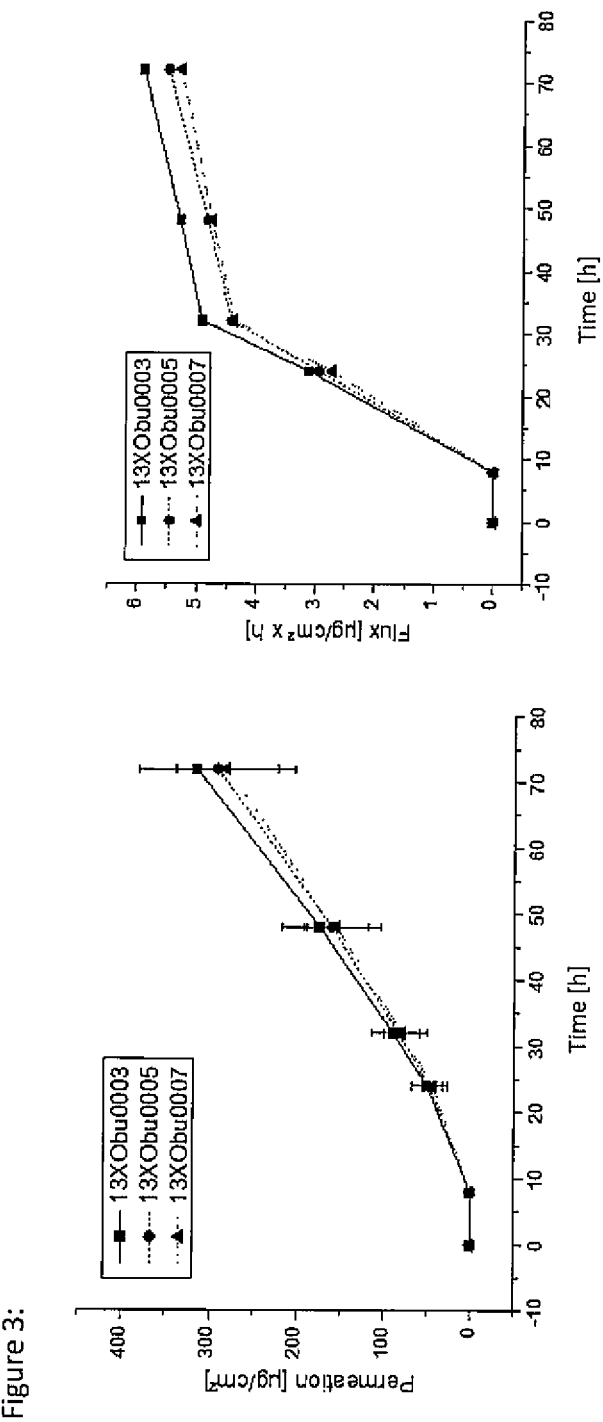

DuroTak: adhesives on the basis of acrylate copolymers (Henkel)
Bio-PSA: adhesives on the basis of silicone (Dow Corning)
Miglyol: Medium-chain triglycerides The in vitro human skin permeation of some of the systems specified in Example 1 was measured using a Franz cell. The substance or formulation (for example gels, salves, solutions, patches) was situated in the donor compartment. The acceptor compartment was filled with buffer or other solutions. The permeation of a substance through the skin could be tracked over the selected time period by taking samples regularly from the acceptor compartment. The use of the Franz cell as diffusion model is suitable especially for predicting the transport of drugs through human skin (=permeation), which corresponds to the systemic availability. It is important to note here that there is no in-vitro in-vivo correlation. In this case, the Franz cell was loaded with human abdominal skin obtained from surgery. 500 μm of dermatomed skin with a diffusion area of 1.165 cm$^2$ was incubated with the transdermal therapeutic system. An aqueous, isotonic phosphate buffer pH=7.4 plus 0.1% sodium azide with a filling volume of 10 mL was used as acceptor medium. The permeation measurement was performed at a temperature of 32° C., with measurements being taken after 3, 6, 8 and 24 hours (n=3). The results of the measurements can be seen in FIGS. 1 to 3.

It can be seen from the drawings that the formulations according to the invention, which forego conventional adhesives, can achieve comparable results to known formulations in respect of active substance permeation and active substance flux.

The invention claimed is:

1. A transdermal therapeutic system, comprising a backing layer impermeable to active substances and a polymer matrix layer on one side of the backing layer impermeable to active substances, wherein the polymer matrix comprises at least one pharmaceutically active substance, at least one inherently non-adhesive polymer, wherein the inherently non-adhesive polymer comprises a polyvinyl caprolactam/polyvinyl acetate/polyethylene glycol copolymer, shellac, a vinylpyrrolidone/vinyl acetate copolymer, hyroxypropyl cellulose, hydroxypropyl methyl cellulose and/or polyvinylpyrrolidone, and the amount of the at least one inherently non-adhesive polymer in the matrix layer is approximately 50 to 90 wt. %, and at least one plasticiser, wherein the at least one plasticizer comprises glycerol and/or polyethylene glycol, the amount of the at least one plasticizer in the matrix layer is approximately 5 to 50 wt. % in relation to the total weight of the matrix layer, characterised in that the polymer matrix is free of inherently adhesive polymers.

2. The transdermal therapeutic system according to claim 1, characterised in that the transdermal therapeutic system does not comprise an additional adhesive layer on the side of the polymer matrix on which the backing layer impermeable to active substance is not situated.

3. The transdermal therapeutic system according to claim 1, characterised in that the inherently adhesive polymer comprises a water-soluble polymer.

4. The transdermal therapeutic system according to claim 1, characterised in that the at least one plasticiser comprises polyethylene glycol 200.

5. The transdermal therapeutic system according to claim 1, characterised in that the at least one pharmaceutically active substance is selected from the group consisting of idebenone, oxybutynin, riociguat, rotigotine, apixaban, ketamine, alendronate and/or fentanyl.

6. The transdermal therapeutic system according to claim 1, characterised in that the amount of the at least one pharmaceutically active substance is from approximately 1 to 20 wt. % in relation to the total weight of the matrix layer.

7. The transdermal therapeutic system according to claim 1, characterised in that the transdermal therapeutic system comprises at least one auxiliary selected from the group comprising dyes, emulsifiers, penetration enhancers, pH regulators, humectants, preservatives and/or antioxidants.

8. A medicinal product comprised of the transdermal therapeutic system according to claim 1.

9. The transdermal therapeutic system according to claim 7, characterised in that the at least one auxiliary is present in an amount of from 0.01 to 20 wt. % in relation to the total weight of the matrix layer.

10. The transdermal therapeutic system of claim 1, wherein the polymer matrix is applied directly to the backing layer comprised of polyethylene terephthalate.

11. The transdermal therapeutic system of claim 1, consisting of the backing layer, the polymer matrix and a removable barrier.

12. The transdermal therapeutic system of claim 1 being adapted for application to a skin of a patient.

13. The transdermal therapeutic system of claim 1 including no (meth)acrylate, poly(meth) acrylate, polyisobutyhene or silicone inclusive polymers.

14. The transdermal therapeutic system according to claim 1, wherein the amount of the at least one inherently non-adhesive polymer in the matrix layer is approximately 60 to 80 wt. % in relation to the total weight of the matrix layer, the at least one plasticiser in the matrix layer is approximately 10 to 30 wt. % in relation to the total weight of the matrix layer, and the weight ratio in parts by weight of the at least one polymer to the at least one plasticiser is approximately 80 to 60 to approximately 20 to 40.

15. The transdermal therapeutic system according to claim 1 including a penetration enhancer selected from pentanoic acid, hexanoic acid, octanoic acid, nonanoic acid, decanoic acid, lauric acid, myristic acid, palmitic acid, stearic acid, arachidic acid, behenic acid, lignoceric acid, isovaleric acid, neoheptanoic acid, neonanonic acid, isostearic acid, oleic acid, palmitoleic acid, linolenic acid, vaccenic acid, petroselinic acid, elaidic acid, oleic acid, arachidonic acid, gadoleic acid, erucic acid, ethyl acetate, methyl propylate, butyl acetate, methyl valerate, diethyl sebacate, methyl laurate, ethyl oleate, isopropyl decanoate, isopropyl myristate (myristic acid isopropyl ester), isopropyl palmitate, and isopropyl oleinate (oleic acid isopropyl ester) and/or esters thereof.

16. The transdermal therapeutic system of claim 15, wherein the penetration enhancer comprises oleic acid and/or acid esters thereof.

* * * * *